US010969374B2

(12) United States Patent
Fu et al.

(10) Patent No.: US 10,969,374 B2
(45) Date of Patent: Apr. 6, 2021

(54) DEVICE AND METHOD FOR LABORATORY ICE JAM AND ICE DAM RADAR MEASUREMENT TESTS

(71) Applicant: CHINA INSTITUTE OF WATER RESOURCES AND HYDROPOWER RESEARCH, Beijing (CN)

(72) Inventors: Hui Fu, Beijing (CN); Xinlei Guo, Beijing (CN); Tao Wang, Beijing (CN); Yongxin Guo, Beijing (CN); Jiazhen Li, Beijing (CN); Ping Ji, Beijing (CN); Jiajia Pan, Beijing (CN); Jinzhi Lu, Beijing (CN)

(73) Assignee: CHINA INSTITUTE OF WATER RESOURCES AND HYDROPOWER RESEARCH, Beijing (CN)

( * ) Notice: Subject to any disclaimer, the term of this patent is extended or adjusted under 35 U.S.C. 154(b) by 0 days.

(21) Appl. No.: 16/905,770

(22) Filed: Jun. 18, 2020

(65) Prior Publication Data
US 2020/0400642 A1    Dec. 24, 2020

(30) Foreign Application Priority Data

Jun. 20, 2019   (CN) .......................... 201910534915.3

(51) Int. Cl.
*G01N 33/18*    (2006.01)
*G01B 7/06*     (2006.01)
*G01S 7/41*     (2006.01)

(52) U.S. Cl.
CPC .............. *G01N 33/18* (2013.01); *G01B 7/06* (2013.01); *G01S 7/418* (2013.01); *G01N 2033/1873* (2013.01)

(58) Field of Classification Search
CPC .. G01B 7/06; G01N 2033/1873; G01N 33/18; G01N 3/317; G01N 3/38;
(Continued)

(56) References Cited

U.S. PATENT DOCUMENTS 3,665,466 A * 5/1972 Hibbard ................. G01N 22/00
                                                        342/59
5,497,100 A * 3/1996 Reiser .................... G01N 22/04
                                                       324/642
(Continued)

FOREIGN PATENT DOCUMENTS

CN       105021791 A     11/2015
CN       106353754 A      1/2017
(Continued)

OTHER PUBLICATIONS

D9: "A double frequency radar system to measure water depth and ice thickness", Shuili Xuebao, vol. 48, No. 11, pp. 1341-1347, Nov. 2017.
(Continued)

*Primary Examiner* — John Fitzgerald
*Assistant Examiner* — Truong D Phan
(74) *Attorney, Agent, or Firm* — J.C. Patents (57) ABSTRACT

The invention relates to a device and method for laboratory ice jam and ice dam radar measurement tests, the device includes a non-metal water tank, a truss spans the top of the non-metal water tank, the truss is connected with a radar plate parallel to a surface of water through a lifting mechanism, a measuring radar is provided on the radar plate, a permeable measuring barrel soaked in the water is provided below the radar plate, a barrel bottom of the permeable measuring barrel is a permeable plate capable of rising and falling, model ice blocks are provided in the permeable measuring barrel, and a handle capable of shaking the truss upwards, downwards, leftwards and rightwards is provided on the truss. According to the invention, through establishing simulated ice jam and ice dam in the permeable measuring barrel, the formation and characteristics of the ice jam and the ice dam are tested, and systematic research can be carried out to address the difficulties, such as radar echo (Continued)

images and the dielectric constant, in the radar measurement of the ice jam and the ice dam and a water depth underneath the ice, so that the measurement accuracy of corresponding equipment is improved, and further development of related disciplines is promoted. A whole set of the device is simple in structure, low in cost, and facilitated and effective in the implementation of tests.

17 Claims, 4 Drawing Sheets (58) Field of Classification Search
CPC .......... G01N 22/00; G01N 3/00; G01N 17/00; G01N 24/00; G01N 2203/005; G01S 7/418

See application file for complete search history.

(56) References Cited

U.S. PATENT DOCUMENTS

| | | | | |
|---|---|---|---|---|
| 5,821,862 A | * | 10/1998 | MacKenzie | B64D 15/20 340/583 |
| 6,049,282 A | * | 4/2000 | MacKenzie | B64D 15/20 340/580 |
| 6,188,348 B1 | * | 2/2001 | Raney | G01S 7/288 342/120 |
| 2009/0217753 A1 | * | 9/2009 | Burris | G01F 23/2962 73/290 V |

FOREIGN PATENT DOCUMENTS

| | | |
|---|---|---|
| CN | 107290744 A | 10/2017 |
| CN | 109784224 A | 5/2019 |
| CN | 109883479 A | 6/2019 |
| JP | H1047819 A | 2/1998 |
| RU | 2551832 C1 | 5/2015 |
| WO | WO9208935 A1 | 5/1992 |

OTHER PUBLICATIONS

D10: "An ice-hydrodynamics simulation platform", Shuili Xuebao, vol. 44, No. 3, pp. 355-360, Mar. 2013.
First Office Action of CN201910534915.3.

* cited by examiner

DEVICE AND METHOD FOR LABORATORY ICE JAM AND ICE DAM RADAR MEASUREMENT TESTS

CROSS-REFERENCE TO RELATED APPLICATIONS

The present application claims priority benefit to Chinese application No. 201910534915.3 filed on Jun. 20, 2019 and entitled "Device and Method for Laboratory Ice Jam and Ice Dam Radar Measurement Tests", the content of which is herewith incorporated by reference in its entirety.

TECHNICAL FIELD

The invention relates to a device and a method for laboratory ice jam and ice dam radar measurement tests, in particular to an experimental test method and device, an experimental method and device for radar measurement of a thickness of the ice jam and the ice dam and a water depth underneath the ice, and also a method and a device for researching and developing ice jam and ice dam radar measurement theories and technologies.

BACKGROUND ART

In winter, the temperature drops, water loses heat, and when the water temperature is reduced below 0 frost appears in a river channel, and then an ice flow is generated. The ice flow is influenced by water flow conditions, topography and wind directions and can accumulate to form an ice cover. When the water flow is at a low speed, the thickness of the ice cover is mainly determined by the thickness of the ice flow solely, and ice flows are sequentially arranged and bound to one another to form a "flat freeze-up"; when the water flow is at a high speed or in an appropriate topographic condition, the ice flow swirls into or gets underneath the ice cover from a front edge thereof to form an ice cover having a large thickness and an extremely uneven surface, whereby an "upright freeze-up" is formed. The process of the generation, development and evolution of the ice may cause the reduction of the water passage capacity of the river channel, and ice jam, ice dam and the like can be easily formed at a river junction, or where the rapid and slow flows join, or where a section of the river channel is suddenly narrowed, and lead to an ice flood disaster.

The rivers in northern China are located in high latitude areas, and various ice flood issues happen in winter, which often causes losses. For example, the Yellow River in China has ice flood hazards almost every year. Before the 1960s, ice flood prevention and disaster mitigation mainly depended on the dike, artificial ice-breaking, blasting, aircraft bombing, cannonball blasting and other measures. After the Sanmenxia water control project and the Liujiaxia hydropower station came into service, under the regulation and storage of the reservoir, the ice flood hazards of the Yellow River were greatly mitigated, but the ice flood issues in the Ningmeng reach of the Yellow River have not yet completely been solved. The Ningmeng reach of the Yellow River has a whole length of about 1217 km, freezes up about 120 days in winter, and has a freeze-up length of generally 800 km, even up to 1200 km in the extreme cases. In the six decades from 1951 to 2010, thirteen years witnessed dike breach disasters due to ice floods, with an average interval of shorter than 5 years. The other river which suffers much from ice floods in China is the Heilongjiang River, which is located between 47-53 degrees north latitude, freezes up for 160-180 days in winter, has a freeze-up length of about 1004 kilometers from the Luoguhe Village of Mohe County to the Hada Village of Sunwu County, and has 22 places where the ice jam and the ice dam often occurs. During the 98 years from 1916 to 2014, twenty-six years witnessed serious ice flood disasters of the Heilongjiang River, an ordinary ice dam was 10-20 km long, the longest could reach 30-50 km, the backwater after the ice dam formation could be as high as 6-8 m, even up to 13 m. In 2009 and 2010, the direct economic losses caused by the Heilongjiang River ice dam amounted to 1,335 and 6,772,000 yuan, respectively. Ice jam and ice dam issues also exist in the project of water diversion from the Yellow River to Qingdao, the project of water diversion from the Yellow River to Tianjin and the middle line of the South-to-North Water Transfer Project, which affect the water supply security in winter. For example, in 2010, the Xiaowangzhuang pumping station was forced to completely shut down because the trash racks were blocked by ice and the water flow was cut off in the water transfer from the Yellow River to Tianjin in winter. On Jan. 29, 2008, in the project of water diversion from the Yellow River to Baiyangdian across the Wei Yunhe Canal, ice dam was formed at the entrance of inverted siphon in a short period of time, which resulted in a blockage of the inverted siphon and the ice jam danger.

Accurate measurement of the thickness of the ice jam and the ice dam and the water depth underneath the ice is a prerequisite for understanding the ice jam and the ice dam disaster and developing relevant disaster mitigation and prevention technologies. However, since the ice jam and the ice dam have the characteristics of multiple voids, irregularities, extremely unstable structural strength and the like, it's difficult, and even dangerous, to measure the prototype of the river channel. Therefore, the existing statistics of the ice jam and the ice dam are very few, hindering further development and improvement of ice prevention and disaster reduction.

With the development of radar technology in recent years, it is now possible to measure the thickness and depth of the ice jam and the ice dam on-site through non-contact radar measurement. However, the first prerequisite of non-contact radar measurement is to have accurate dielectric constants of the ice jam and the ice dam and the water underneath the ice, as well as clearly discernable radar echo images, and these parameters are mainly affected by the porosity of the ice jam and the ice dam and riverbed conditions. The dielectric constants of the ice jam and the ice dam and the water underneath the ice can be measured and calibrated by field prototype artificial drilling on the surface of the ice, but the safety issue is a concern as described above; the definition of radar echo images depends on radar frequency and algorithm, and the field test costs much.

SUMMARY OF THE INVENTION

It's an object of the invention to overcome the shortcomings of the prior art by providing a device and a method for laboratory ice jam and ice dam radar measurement tests. According to the device and the method, a real environment is simulated by the device in a laboratory, the ice jam and the ice dam are measured by non-contact radar equipment, interference of unnecessary factors is eliminated, and research and development of river ice measurement theories and ice prevention and disaster mitigation technologies can be promoted.

The object of the invention is realized by the following technical solution: A device for laboratory ice jam and ice dam radar measurement tests, comprising: a non-metal water tank and a truss spanning the top of the water tank, wherein the truss is connected with a radar plate parallel to a surface of water through a lifting mechanism, a measuring radar is provided on the radar plate, a permeable measuring barrel soaked in the water is provided below the radar plate, a barrel bottom of the permeable measuring barrel is a permeable plate capable of rising and falling, and model ice blocks are provided in the permeable measuring barrel; a handle capable of shaking the truss upwards, downwards, leftwards and rightwards is provided on the truss.

Furthermore, the water tank has a rectangular horizontal projection, and a water depth scale is provided on a sidewall.

Furthermore, the truss is in a pound sign shape, and eight ends of the truss are respectively provided with pulleys borne on a guide rail.

Furthermore, the lifting mechanism is a screw rod and a nut.

Furthermore, the horizontal projections of the radar platform and the permeable measuring barrel are rectangular, a barrel wall is composed of four perforated plates, the barrel bottom is composed of one perforated plate, and a diameter of a pore in the perforated plate is smaller than 0.5 times of an average particle diameter of a model ice block.

Furthermore, the four perforated plates composing the barrel wall are connected by four vertical supporting beams provided with a range scale thereon.

Furthermore, the supporting beam is provided with a clamping groove extending in a length direction and insertable into an edge of the perforated plate.

Furthermore, the edge of the barrel bottom perforated plate is provided with a traction rope capable of pulling the barrel bottom perforated plate upwards and downwards.

Furthermore, the model ice blocks are polyethylene blocks.

A method for laboratory ice jam dam radar measurement tests using the device, comprising the steps of:

step 1, preparing model ice blocks: preparing various model ice blocks of different sizes by using polyethylene having a similar density to natural ice blocks;

step 2, providing a medium at the bottom of the water tank: paving pebbles, silt or a mixture of pebbles and silt at the bottom of the water tank according to an experimental scheme, and skipping this step if the experimental scheme does not require paving any medium at the bottom of the water tank;

step 3, setting water depths and model ice blocks: injecting water into the water tank or adjusting water depths by using the water depth scale according to an experiment requirement, putting one or more types of model ice blocks mixed at a certain ratio into the permeable measuring barrel, pulling up the traction rope to enable the barrel bottom to reach the vicinity of a target position, and calculating a volume of the model ice blocks V1 through weighing and density conversion before the model ice blocks are placed in the permeable measuring barrel;

step 4, deploying equipment: putting the truss, the lifting mechanism, the radar plate, the permeable measuring barrel and the model ice blocks into the water tank;

step 5, adjusting porosities of the model ice blocks: repeatedly vibrating a test platform back and forth, leftwards and rightwards, and upwards and downwards through the guide mil to enable the model ice blocks to uniformly accumulate in the perforated plate, slightly adjusting the barrel bottom through the traction rope to enable the bottom of the ice jam and ice dam model simulated by floating model ice blocks to be even, recording a thickness of the ice jam and ice dam model at the moment, measuring a total volume V2 in the barrel and the water depth underneath the ice, and calculating the porosity V1/V2 of the current ice jam and ice dam model;

step 6, radar measurement: putting the radar into the radar plate, adjusting the radar plate through the lifting mechanism to enable the radar plate to be as close to the surface of the water as possible, starting the radar to measure, recording a measurement result, comparing and analyzing an error between a radar measurement value and a field measurement value, and further analyzing variation characteristics of a radar echo image and a dielectric constant; and step 7, adjusting experimental conditions or ending the experiment: alternatively, returning to step 2, performing systematic repeated and comparative experiments using different porosities, ice block sizes and water depths underneath the ice, or ending the experiment.

The invention has the following advantageous effects: according to the invention, a simulated ice jam and ice dam model is established in a permeable measuring barrel, the formation and characteristics of the ice jam and the ice dam are tested, systematic theoretical research can be carried out to address the difficulties, such as radar echo images and dielectric constants, in the radar measurement of the ice jam and the ice dam to improve the measurement accuracy of corresponding equipment and promote further development of related disciplines. A whole set of the device is simple in structure, low in cost, and facilitated and effective in the implementation of tests, compared with the conventional field measurement, the risks, expenses and costs of measurement can be greatly reduced, and the measurement accuracy is improved. The invention can not only be used for researching the influence of the porosity of the ice jam and the ice dam and the riverbed condition on the dielectric constant, but also be used for testing radar echo images under different conditions, thereby enriching the theories of the radar measurement of the ice jam and the ice dam and the water underneath the ice, and providing a key basis for accurate field radar measurement of the prototype.

BRIEF DESCRIPTION OF THE DRAWINGS

The invention is further illustrated below in conjunction with the accompanying drawings and embodiments.

DETAILED DESCRIPTION OF THE INVENTION

Embodiment 1

Figure 1:
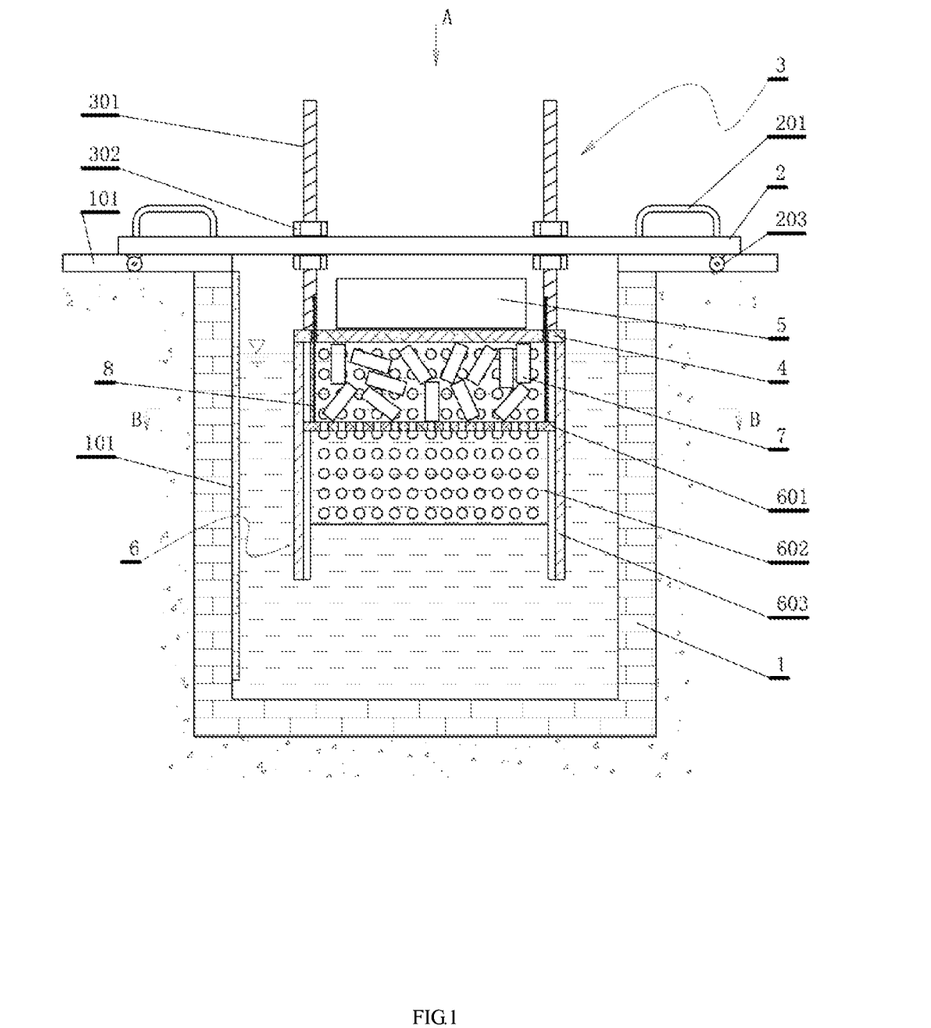
FIG. 1 is a schematic view showing a structure of the device described in Embodiments 1, 2, 3, 4, 5, 6 and 8 of the present invention.

The embodiment is a device for laboratory ice jam and ice dam radar measurement tests shown in FIG. 1. This embodiment includes a non-metal water tank 1, a truss 2 spans the top of the water tank, the truss is connected with a radar plate 4 parallel to a surface of water through a lifting mechanism 3, a measuring radar 5 is provided on the radar plate, a permeable measuring barrel 6 soaked in water is provided below the radar plate, a barrel bottom 601 of the permeable measuring barrel is a permeable plate capable of rising and falling, model ice blocks 7 are provided in the permeable measuring barrel, and a handle 201 capable of shaking the truss upwards, downwards, leftwards and rightwards is provided on the truss.

The water tank in the embodiment can be designed as having a square horizontal projection, for example, a water tank having a 2*2*2 m square projection, and the water tank is made of a brick-concrete structure without steel to prevent the influence of strong radar echo signals of the steel on the ice jam and the ice dam measurement, and a water tank with a circular horizontal projection can be adopted. The top of the water tank can also be provided with a sliding rail, so that a test platform for placing the radar can move back and forth, leftwards and rightwards. The main function of the water tank is to simulate different water depths underneath the ice and different riverbeds, such as a pebbled riverbed, a silt riverbed and the like, through an arranged scale.

The whole test device also includes a truss, a handle provided on the truss, a supporting beam (a guide rail), a permeable measuring barrel, a lifting mechanism and the like.

The truss spans the top of a wall of the water tank, so that experimental equipment such as radar and a measuring barrel can be controlled on the surface of or at a proper position in the water. The truss may also take many forms, such as a cruciform truss, or a pound-sign-shaped truss, etc. An upper handle of the truss is used for enabling the model ice blocks to be uniformly accumulated in the permeable measuring barrel through repeated vibration back and forth, leftwards and rightwards, and upwards and downwards, so that the influence of the porosity of the ice jam on the radar measurement accuracy can be the focus during the test, and the influence of variety and complexity of influential factors on data analysis can be avoided.

The radar measurement plate is used for bearing the radar. The radar measurement plate must be non-metallic to avoid blocking radar waves incident into the water. In the experiment, the radar measurement plate should be as close to the surface of the water as possible to improve the radar echo intensity. Because different water levels underneath the ice need to be simulated in the experiment, the radar measurement platform needs to be lifted and lowered from time to time, so the lifting mechanism is provided. There are various options of the lifting mechanism, such as a lifting mechanism adopting a screw rod and a fixed nut, in which case the position of the radar can be adjusted upwards and downwards according to different water levels by lifting and lowering the screw rod and the fixed nut.

The permeable measuring barrel is a key facility, functioning to aggregate the simulating ice blocks together to form simulated ice jam and ice dam with a certain porosity, so as to analyze and study the radar measurement theoretically.

The permeable measuring barrel must also be non-metallic and can take various forms, such as being surrounded by a non-metallic mesh or being formed by splicing several perforated plates. The horizontal projection of the permeable measuring barrel may be circular or square. The bottom of the permeable measuring barrel should be capable of moving upwards and downwards so as to simulate different porosity conditions of the ice jam and the ice dam and render a flat bottom of the simulated ice jam, whereby the thickness of the ice jam and the ice dam features a constant value, and thus related research about mechanisms can be performed.

Embodiment 2

This embodiment is an improvement to Embodiment 1 with respect to the water tank. The water tank according to this embodiment has a rectangular horizontal projection, and a water depth scale 101 is provided on a side wall, as shown in FIGS. 1 and 2.

Figure 2:
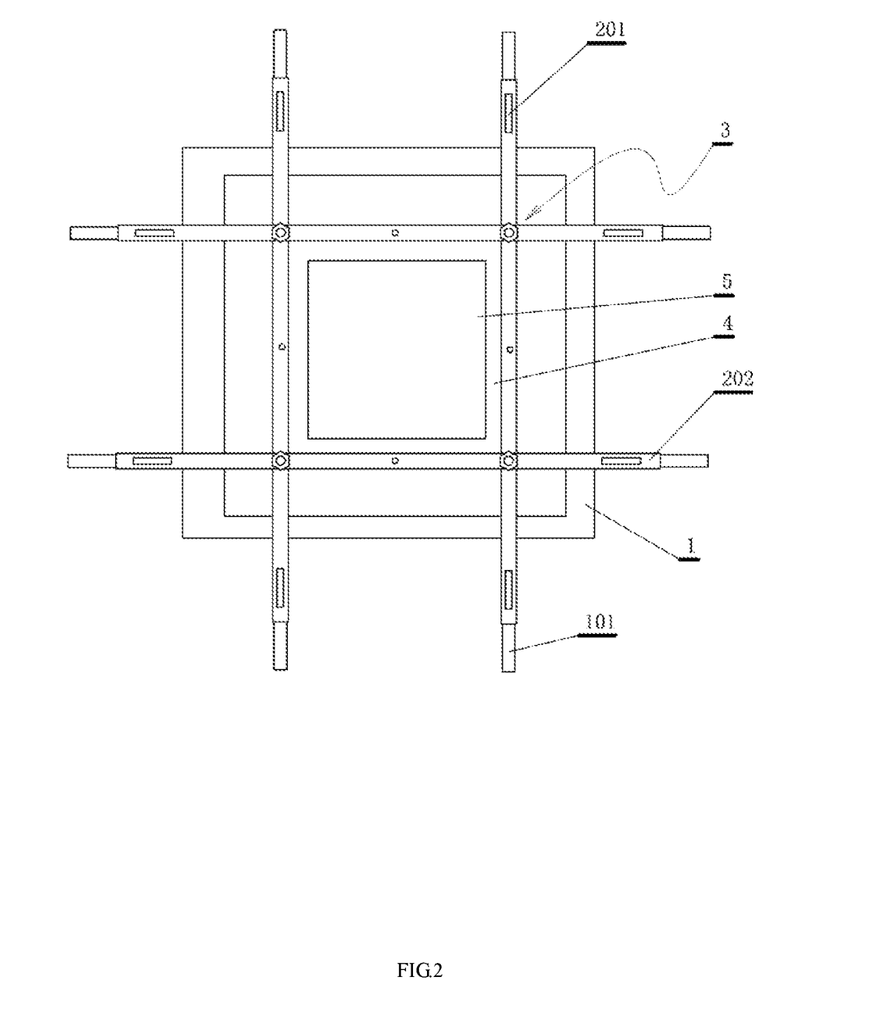
FIG. 2 is a schematic view, from a direction A in FIG. 1, showing a structure of a pound-sign-shaped truss, a radar and a radar plate according to Embodiments 2 and 3 of the present invention.

The water tank according to this embodiment is square, as shown in FIG. 2, and the sidewall of the water tank can be made of bricks and lined with cement and waterproof materials.

The water depth scale is used to facilitate reading the depth of the water as it is being filled, so as to obtain water depth data during the experiment.

Embodiment 3

This embodiment is an improvement to the embodiments described above with respect to the truss. The truss of this embodiment is in a pound sign shape, and eight ends 202 of which are respectively provided with pulleys 203 borne on the guide rail 101, as shown in FIGS. 1 and 2.

By landing pulleys in different directions, the pound-sign-shaped truss can shake back and forth, leftwards and rightwards. The pulleys can be directly borne on the edge of the water tank or on the guide rail disposed on the edge of the water tank.

Embodiment 4

This embodiment is an improvement to the above-described embodiments with respect to the lifting mechanism. The lifting mechanism described in this embodiment is a screw rod 301 and a nut 302, as shown in FIG. 1.

The lifting mechanism in this embodiment adopts a long screw rod, and uses an upper nut and a lower nut for locking the radar plate at a position on the screw rod, when the position of the radar platform needs to be changed, it's only necessary to loosen one nut, adjust the other nut to a required position, and then fix the radar plate with the loosened nut. Such a lifting mechanism is simple and effective.

Embodiment 5

Figure 3:
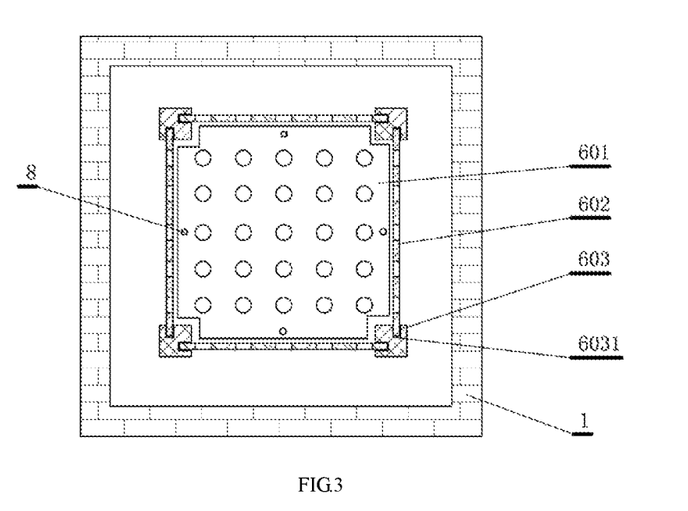
FIG. 3 is a cross-sectional view, taken along B-B in FIG. 1, showing a structure of a permeable measuring barrel according to Embodiments 5, 6, and 7 of the present invention.

This embodiment is an improvement to the embodiments described above with respect to the radar platform and permeable measuring barrel. The horizontal projections of the radar platform and the permeable measuring barrel in this embodiment are rectangular, the barrel wall is composed of four perforated plates 602, the barrel bottom is composed of one perforated plate, and a diameter of a pore in the perforated plate is smaller than 0.5 times of the average particle diameter of a model ice block, as shown in FIGS. 1 and 3.

The permeable measuring barrel in this embodiment is square and is composed of four side plates and a bottom plate (barrel bottom). The side plate and the barrel bottom are both perforated plates and have water permeability. The four side plates may be fixedly joined, for example, bounded by glue. In order to facilitate the replacement by those of different pore diameters, the four perforated plates can be bonded together using supporting beams with clamping grooves. When the perforated plate needs to be replaced, it's only necessary to draw the perforated plate out along the clamping groove and insert a new perforated plate along the clamping groove.

If the model ice blocks used in the test have the same particle diameter, the diameter of the pore in the perforated plate should be smaller than the minimum outer profile of the model ice block to prevent the model ice block from floating outside the perforated plate; in the case of spherical model ice blocks, the diameter of the pore in the perforated plate should be smaller than the diameter of the sphere. In the case of rectangular model ice blocks, the diameter of the pore in the perforated plate should be smaller than the smallest 3-dimensional diagonal line. If the model ice blocks used in the experiment are a mixture of model ice blocks with different particle diameters, in order to prevent ice from escaping during repeated vibration, the diameter of the pore in the perforated plate should be less than 0.5 times of the average particle diameter of the model ice block according to long-term research statistics. In the case of spherical model ice blocks, the diameter of the pore in the perforated plate should be less than 0.5 times the diameter of the sphere. In the case of rectangular model ice blocks, the diameter of the pore in the perforated plate should be less than 0.5 times the smallest 3-dimensional diagonal line.

Embodiment 6

This embodiment is an improvement to the embodiments described above with respect to the permeable measuring barrel. The four perforated plates composing the barrel wall according to this embodiment are connected by four vertical supporting beams 603 provided with a range scale thereon, as shown in FIGS. 1 and 3.

The supporting beam with the clamping groove is used for fixing the side plates around and enabling the sliding bottom plate to slide upwards and downwards along the supporting beam under the action of a traction rope, and the perforated side plate is used for discharging or letting in the water when the perforated sliding bottom plate slides upwards and downwards.

The range scale on the supporting beam is graduated lines and range marks on the supporting beam, and the graduated lines and range marks can show the specific lifted and lowered positions of the barrel bottom perforated plate for recording.

Embodiment 7

This embodiment is an improvement to the embodiments described above with respect to the supporting beam. The supporting beam is provided with a clamping groove 6031 extending in the length direction and insertable into the edge of the perforated plate, as shown in FIG. 3.

The clamping groove is elongated, having a length equal to the length of the supporting beam and a width equal to the thickness of the side plate of the permeable measuring barrel, and the edge of the side plate can be inserted into the clamping groove.

Embodiment 8

This embodiment is an improvement to the embodiments described above with respect to the barrel bottom perforated plate. The edge of the barrel bottom perforated plate according to this embodiment is provided with a traction rope 8 capable of pulling the barrel bottom perforated plate upwards and downwards, as shown in FIG. 1.

Since the porosity of the model ice blocks needs to be adjusted through repeated vibration before the measurement starts in the experiment, the position of the barrel bottom perforated plate is adjusted by tightening the rope, which is most convenient and lowest in cost.

Embodiment 9

This embodiment is an improvement to the embodiments described above with respect to the model ice blocks. The model ice blocks described in this example are polyethylene blocks.

The density of polyethylene is approximately 917 kg/m$^3$, quite similar to the density of ice, and the model ice block can be taken as a rectangular body or a sphere to facilitate calculation of the volume. However, the sphere costs more than the rectangular body does because the latter can be directly cut from a polyethylene plate.

Embodiment 10

This embodiment is a method for laboratory ice jam and ice dam radar measurement tests using the device described in the above embodiments.

The theoretical basis of the test method in this embodiment is as follows:

the two-way travel time of the radar measurement of the thickness of the ice and the water depth can be calculated according to the following equation:

$$t = \frac{\sqrt{d^2 + 4H^2}}{v};$$

where H is the thickness of the ice or the water depth, v is a propagation velocity of an electromagnetic wave in ice or water, and d is the distance between a transmitting antenna and a receiving antenna of the radar.

The propagation velocity v of the electromagnetic wave in ice or water relates to the dielectric constant and can be calculated according to the following equation:

$$v = \frac{c}{\sqrt{\varepsilon}};$$

where c is a propagation velocity of an electromagnetic wave in a vacuum, which is 30 cm/ns; and E is the dielectric constant.

It can be learned from the above equation that an equation for calculating the thickness of the ice and the water depth during the radar measurement is as follows:

$$H = \sqrt{\frac{c^2 t^2 - \varepsilon d^2}{4\varepsilon}}.$$

Therefore, the major factors determining the radar measurement accuracy are as follows:

(1) whether the radar echo image is clear enough to acquire an accurate two-way travel time t; and (2) the value of the dielectric constant E of the ice jam and the ice dam under the conditions of different thicknesses of the ice, water depths and porosities.

The dielectric constant of pure ice or water is constant, and generally, the ice and the water in nature are more or less mixed with other impurities, so that the dielectric constant of the ice in nature is 3-4, and the dielectric constant of the water is about 78-82. The difficulty of the measurement of the ice jam and the ice dam lies in the ice-water mixture state, radar echo images on ice-water interface are not clear enough, and the dielectric constant of the ice jam and the ice dam changes with different porosities because of the large difference between dielectric constants of ice and water. The method provided by this embodiment can render a systematic test and research to address the difficulty in radar measurement of the ice jam and the ice dam, so that the measurement accuracy of corresponding equipment is improved, and further development of relevant disciplines is promoted.

According to this embodiment, the porosity is changed by using the permeable measuring barrel in such a manner that model ice blocks with a known solid volume V1 are mixed and placed in the permeable measuring barrel; the barrel wall, the radar platform close to the surface of the water and the barrel bottom enclose the model ice blocks in a given space V2, wherein the given space is an ice jam and ice dam model; and the ratio of the solid volume of the ice blocks to the volume of the ice jam and ice dam model, i.e., V1/V2, is the porosity of the ice jam and ice dam model.

In actual operation, the sidewall of the permeable measuring barrel is fixed, the radar platform close to the surface of the water is also fixed, and V2 can be changed only by moving the barrel bottom upwards and downwards. A common design in an experimental scheme includes: setting a plurality of porosities, setting V1 and V2 according to the porosities, generally weighing and calculating a selected number of model ice blocks, and selecting a position of the barrel bottom according to V1 and the porosities, wherein the position is a target position of the barrel bottom.

In an actual experiment, it is usually necessary to set a plurality of porosities to measure the dielectric constant of the ice jam and the ice dam under various conditions by radar.

Figure 4:
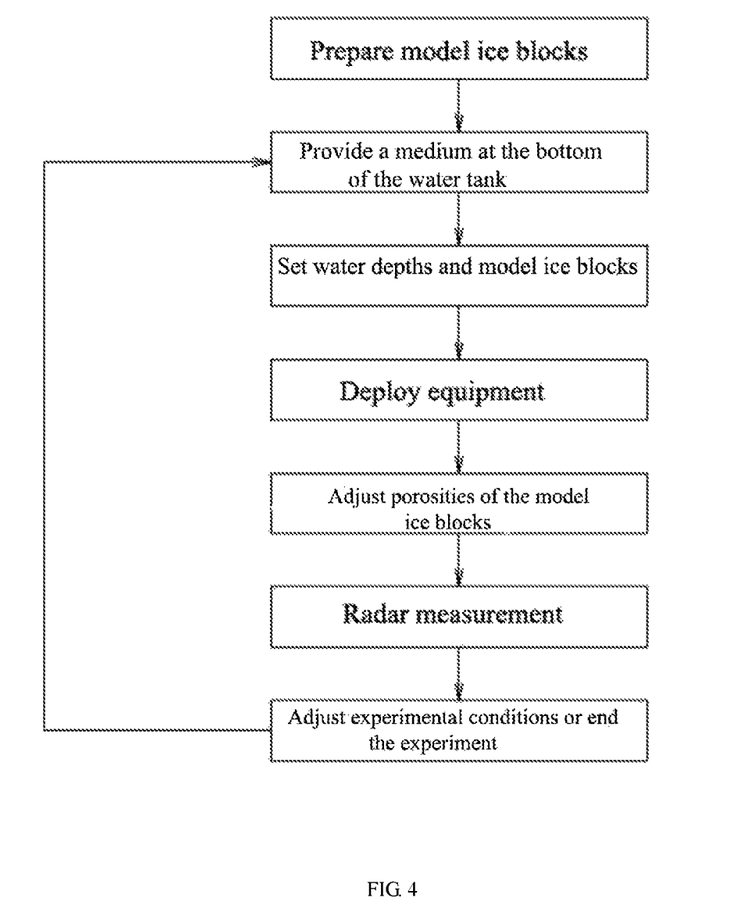
FIG. 4 is a flow chart of a method according to Embodiment 10 of the present invention.

The method in this embodiment, as shown in FIG. 4, includes the steps of:

step 1, making model ice blocks: preparing various model ice blocks of different sizes by using polyethylene having a similar density to natural ice blocks; wherein the purpose of preparing various model ice blocks is to simulate the porosities of the ice jam and the ice dam under different conditions;

step 2, providing a medium at the bottom of the water tank: paving pebbles, silt or a mixture of pebbles and silt at the bottom of the water tank according to the experimental scheme, and skipping this step if the experimental scheme does not require paving any medium at the bottom of the water tank; wherein media, such as pebbles and silt, are not paved or paved at the bottom of the water tank according to the experimental scheme to simulate different riverbed media conditions in real field situations;

step 3, setting water depths and model ice blocks: injecting water into the water tank or adjusting the water depth by using the water depth scale according to the experiment requirement, putting one or more types of model ice blocks mixed at a certain ratio into the permeable measuring barrel, pulling up the traction rope to enable the barrel bottom to reach the vicinity of the target position, and calculating the volume of the current model ice blocks V1 through weighing and density conversion before the model ice blocks are placed in the permeable measuring barrel; wherein water is injected into the water tank until reaching a certain depth to simulate radar reflections at different depths and analyze the reflection characteristics of radar waves in the water and the ice jam and the ice dam, the target position refers to a position of the barrel bottom when V2 required in this experiment is reached, in general, due to the mixed state of the simulating ice blocks, the target position cannot be reached at one try, oscillation in water is necessary to activate the mixed model ice blocks, so that the target position can be really reached;

step 4, deploying equipment: putting the truss, the lifting mechanism, the radar plate, the permeable measuring barrel and the model ice blocks into the water tank;

step 5, adjusting the porosity of the model ice blocks: repeatedly vibrating the test platform back and forth, leftwards and rightwards, and upwards and downwards through the guide mil to enable the model ice blocks to uniformly accumulate in the perforated plate, slightly adjusting the barrel bottom through the traction rope to enable the bottom of the ice jam and ice dam model simulated by floating model ice blocks to be even, recording the thickness of the ice jam and ice dam model at the moment, measuring the total volume V2 in the barrel and the water depth underneath the ice, and calculating the porosity V1/V2 of the current ice jam and ice dam model; wherein this step is implemented for rendering uniform voids among the model ice blocks to study the influence of a single factor on radar detection, V1 is the volume of the model ice blocks when arranged orderly without any void among the ice blocks, and V2 is the volume of the model ice blocks in the permeable measuring barrel when in a mixed state with voids among the ice blocks; in the actual experiment, the preset porosity can be changed according to the experimental requirement, therefore, it would be enough either the barrel bottom can accurately reach the target position, or the bottom of the ice jam and ice dam model is flattened by the barrel bottom according to actual situations, and the position of the barrel bottom is recorded to calculate the porosity V1/V2;

step 6, radar measurement: putting the radar into the radar plate, adjusting the radar plate through the lifting mechanism to enable the radar plate to be as close to the surface of the water as possible, starting the radar to measure, recording a measurement result, comparing and analyzing an error between a radar measurement value and a field measurement value, and further analyzing variation characteristics of the radar echo image and the dielectric constant; wherein the purpose of enabling the radar plate as close to the surface of the water as possible is to enhance the radar echo signal, the water depth H and the echo time t of the radar are recorded, and the dielectric constants E of the simulated ice jam and ice dam and the water underneath the ice are calculated according to the following equation:

$$\varepsilon = \left(\frac{ct}{2H}\right)^2;$$

where c is the propagation velocity of the electromagnetic wave in the vacuum; and step 7, adjusting experimental conditions or ending the experiment: alternatively, returning to step 2, performing systematic repeated and comparative experiments using different porosities, ice block sizes and water depths underneath the ice, or ending the experiment; wherein it is necessary to carry out simulation experiments with a plurality of groups of model ice blocks having different sizes, compare and analyze to draw a correct conclusion, multiple times of detection are necessary to obtain accurate results even if the model ice blocks are the same.

Finally, it should be noted that the above description is only intended to illustrate the technical solution of the present invention and not to limit the same, and although the present invention is described in detail with reference to a preferred arrangement, it should be understood by those skilled in the art that modifications and equivalent substitutions may be made to the technical solution of the present invention, such as the structural form of the device, the form of the model ice block, the sequence of steps and the like without departing from the spirit and scope of the technical solution of the present invention.

The invention claimed is:

1. A device for laboratory ice jam and ice dam radar measurement tests, comprising: a non-metal water tank and a truss spanning a top of the water tank, wherein the truss is connected with a radar plate parallel to a surface of water through a lifting mechanism, a measuring radar is provided on the radar plate, a permeable measuring barrel soaked in the water is provided below the radar plate, a barrel bottom of the permeable measuring barrel is a permeable plate capable of rising and falling, and model ice blocks are provided in the permeable measuring barrel; a handle capable of shaking the truss upwards, downwards, leftwards and rightwards is provided on the truss.

2. The device according to claim 1, wherein the model ice blocks are polyethylene blocks.

3. The device according to claim 1, wherein the water tank has a rectangular horizontal projection, and a water depth scale is provided on a sidewall.

4. The device according to claim 3, wherein the model ice blocks are polyethylene blocks.

5. The device according to claim 3, wherein the truss is in a pound sign shape, and eight ends of the truss are respectively provided with pulleys borne on a guide rail.

6. The device according to claim 5, wherein the model ice blocks are polyethylene blocks.

7. The device according to claim 5, wherein the lifting mechanism is a screw rod and a nut.

8. The device according to claim 7, wherein the model ice blocks are polyethylene blocks.

9. The device according to claim 7, wherein horizontal projections of the radar plate and the permeable measuring barrel are rectangular, a barrel wall is composed of four perforated plates, the barrel bottom is composed of one perforated plate, and a diameter of a pore in the perforated plate is smaller than 0.5 times of an average particle diameter of a model ice block.

10. The device according to claim 9, wherein the model ice blocks are polyethylene blocks.

11. The device according to claim 9, wherein the four perforated plates composing the barrel wall are connected by four vertical supporting beams provided with a range scale thereon.

12. The device according to claim 11, wherein the model ice blocks are polyethylene blocks.

13. The device according to claim 11, wherein each of the four vertical supporting beams is provided with a clamping groove extending in a length direction and insertable into an edge of a corresponding one of the four perforated plates, respectively.

14. The device according to claim 13, wherein the model ice blocks are polyethylene blocks.

15. The device according to claim 13, wherein an edge of the one perforated plate of the barrel bottom is provided with a traction rope capable of pulling the barrel bottom perforated plate upwards and downwards.

16. The device according to claim 15, wherein the model ice blocks are polyethylene blocks.

17. A method for laboratory ice jam and ice dam radar measurement tests using the device according to claim 1, comprising the steps of:

step 1, preparing model ice blocks: preparing various model ice blocks of different sizes by using polyethylene having a similar density to natural ice blocks;

step 2, providing a medium at the bottom of the water tank: paving pebbles, silt or a mixture of pebbles and silt at the bottom of the water tank according to an experimental scheme, and skipping this step if the experimental scheme does not require paving any medium at the bottom of the water tank;

step 3, setting water depths and model ice blocks: injecting water into the water tank or adjusting water depths by using the water depth scale according to an experiment requirement, putting one or more types of model ice blocks mixed at a certain ratio into the permeable measuring barrel, pulling up the traction rope to enable the barrel bottom to reach the vicinity of a target position, and calculating a volume of the model ice blocks V1 through weighing and density conversion before the model ice blocks are placed in the permeable measuring barrel;

step 4, deploying equipment: putting the truss, the lifting mechanism, the radar plate, the permeable measuring barrel and the model ice blocks into the water tank;

step 5, adjusting porosities of the model ice blocks: repeatedly vibrating the test platform back and forth, leftwards and rightwards, and upwards and downwards through the guide rail to enable the model ice blocks to uniformly accumulate in the perforated plate, slightly adjusting the barrel bottom through the traction rope to enable the bottom of the ice jam and ice dam model simulated by floating model ice blocks to be even, recording a thickness of the ice jam and ice dam model at the moment, measuring a total volume V2 in the barrel and the water depth underneath the ice, and calculating porosity V1/V2 of the current ice jam and ice dam model;

step 6, radar measurement: putting the radar into the radar plate, adjusting the radar plate through the lifting mechanism to enable the radar plate to be as close to the surface of the water as possible, starting the radar to measure, recording a measurement result, comparing and analyzing an error between a radar measurement value and a field measurement value, and further analyzing variation characteristics of a radar echo image and a dielectric constant; and step 7, adjusting experimental conditions or ending the experiment: alternatively, returning to step 2, performing systematic repeated and comparative experiments using different porosities, ice block sizes and water depths underneath the ice, or ending the experiment.

* * * * *